US00RE36000E

United States Patent [19]

Swedlow et al.

[11] E Patent Number: Re. 36,000

[45] Reissued Date of Patent: Dec. 22, 1998

[54] ADHESIVE PULSE OXIMETER SENSOR WITH REUSABLE PORTION

[75] Inventors: David B. Swedlow, Danville; Russell DeLonzor, Union City; Jessica Warring, Millbrae, all of Calif.

[73] Assignee: Nellcor Puritan Bennett Incorporated, Hayward, Calif.

[21] Appl. No.: 437,964

[22] Filed: May 10, 1995

Related U.S. Patent Documents

Reissue of:

[64] Patent No.: 5,209,230
Issued: May 11, 1993
Appl. No.: 741,290
Filed: Aug. 6, 1991

U.S. Applications:

[63] Continuation-in-part of Ser. No. 600,541, Oct. 19, 1990, abandoned.

[51] Int. Cl.[6] ..... A61B 5/02

[52] U.S. Cl. ..... 128/633; 128/637; 128/664; 128/665; 356/41

[58] Field of Search ..... 128/633, 637, 128/664, 665; 606/13; 356/39–41

[56] References Cited

U.S. PATENT DOCUMENTS

| | | | |
|---|---|---|---|
| 3,167,658 | 1/1965 | Richter | 250/239 |
| 3,599,629 | 8/1971 | Gordy | 128/2.06 E |
| 3,602,213 | 8/1971 | Howell et al. | 128/2.05 F |
| 3,617,374 | 11/1971 | Hodson et al. | 117/212 |
| 3,769,974 | 11/1973 | Smart et al. | 128/2.05 P |
| 3,807,388 | 4/1974 | Orr et al. | 128/205 R |
| 4,013,067 | 3/1977 | Kresse et al. | 128/2.05 R |
| 4,091,803 | 5/1978 | Pinder | 128/2.05 P |
| 4,305,401 | 12/1981 | Reissmueller et al. | 128/690 |
| 4,350,165 | 9/1982 | Striese | 128/640 |
| 4,370,984 | 2/1983 | Cartmell | 128/640 |
| 4,380,240 | 4/1983 | Jöbsis et al. | 128/633 |
| 4,406,289 | 9/1983 | Wesseling et al. | 128/670 |
| 4,611,601 | 9/1986 | Bowman | 128/673 |
| 4,644,092 | 2/1987 | Gentry | 174/36 |
| 4,653,498 | 3/1987 | New, Jr. et al. | 128/633 |
| 4,653,501 | 3/1987 | Cartmell et al. | 128/640 |
| 4,700,708 | 10/1987 | New, Jr. et al. | 128/633 |
| 4,824,242 | 4/1989 | Frick et al. | 356/41 |
| 4,825,879 | 5/1989 | Tan et al. | 128/633 |
| 4,830,014 | 5/1989 | Goodman et al. | 128/665 |
| 4,834,532 | 5/1989 | Yount | 356/41 |
| 4,848,335 | 7/1989 | Manes | 128/303 |
| 4,863,757 | 9/1989 | Durand | 427/47 |
| 4,865,038 | 9/1989 | Rich et al. | 128/633 |
| 4,867,165 | 9/1989 | Noller et al. | 128/633 |
| 4,928,691 | 5/1990 | Nicolson et al. | 128/633 |
| 4,960,614 | 10/1990 | Durand | 427/54.1 |
| 4,964,408 | 10/1990 | Hink et al. | 128/633 |
| 5,006,397 | 4/1991 | Durand | 428/209 |
| 5,036,128 | 7/1991 | Durand | 524/440 |
| 5,047,260 | 9/1991 | Durand | 427/54.1 |
| 5,061,551 | 10/1991 | Durand | 428/209 |
| 5,069,213 | 12/1991 | Polczynski | 128/665 |
| 5,080,098 | 1/1992 | Willett et al. | 128/633 |
| 5,090,410 | 2/1992 | Saper et al. | 128/664 |
| 5,094,240 | 3/1992 | Muz | 128/633 |
| 5,193,547 | 3/1993 | Evans, II et al. | 128/668 |
| 5,209,230 | 5/1993 | Swedlow et al. | 128/633 |
| 5,261,415 | 11/1993 | Dussault | 128/719 |

FOREIGN PATENT DOCUMENTS

| | | | |
|---|---|---|---|
| 671279 | 10/1963 | Canada | 128/2 |
| 0019478 | 11/1980 | European Pat. Off. . | |
| 0284943 | 10/1988 | European Pat. Off. . | |
| 2348992 | 4/1974 | Germany . | |
| WO8909566 | 10/1989 | WIPO . | |

*Primary Examiner*—Brian L. Casler
*Attorney, Agent, or Firm*—Rothwell, Figg, Ernst & Kurz

[57] ABSTRACT

A pulse oximeter sensor that is designed to surround an appendage of the patient, such as a finger, toe or foot is disclosed. The sensor has a reusable member which preferably includes a photodetector. A disposable, flexible member preferably contains the photoemitter and can be wrapped around the patient's appendage to secure it to the appendage and the reusable member. When secured, the photoemitter and photodetector end up on opposite sides of the appendage. The disposable member connects to the reusable member to establish electrical contact. The reusable member is connected to a cable which can be plugged into a sensor monitoring system.

27 Claims, 2 Drawing Sheets

ADHESIVE PULSE OXIMETER SENSOR WITH REUSABLE PORTION

Matter enclosed in heavy brackets [ ] appears in the original patent but forms no part of this reissue specification; matter printed in italics indicates the additions made by reissue.

BACKGROUND OF THE INVENTION

This is a continuation-in-part of patent application Ser. No. 07/600,541, filed Oct. 19, 1990, now abandoned.

This invention relates to sensors for use with noninvasive pulse monitors such as plethysmographs or pulse oximeters.

A plethysmograph is a pulse monitor The plethysmograph sensor shines light into the patient's tissue, and the light transmitted through the tissue is received by a photodetector. The photodetector generates electrical signals corresponding to the transmitted light levels and transmits the signals to a monitor for processing. Arterial blood will absorb some of the light, with more light being absorbed when there is more blood. Thus, changes in the amount of transmitted light are related to pulses of arterial blood in the illuminated tissue.

A pulse oximeter is a device for noninvasively determining the oxygen saturation of arterial blood. The pulse oximeter sensor shines light at two different wavelengths (one in the red range, the other in the infrared range) through a portion of the patient's blood-perfused tissue. The red and infrared light transmitted through the tissue is detected by a photodetector. The amount of light absorbed varies with the amount of oxygen in the blood, and varies differently for red and infrared light. The pulse oximeter monitor computes blood oxygen saturation based on the changes in the two detected light levels between two points in time.

There are several types of sensors for plethysmographs and pulse oximeters. One is a surface sensor in which the light emitter and the photodetector are mounted on the same sensor face. The sensor is attached to the patient with both the light emitter and the detector on the same side of the patient's appendage (e.g., on the patient's forehead). This type of sensor detects light reflected back from the tissue, rather than light transmitted through an appendage. The signal detected will thus be weaker in most cases. The sensor is typically attached with a strap, headband or tape over the sensor, or an adhesive pad between the sensor and the skin.

Another type of sensor is a clamp design, such as that described in U.S. Pat. No. 4,685,464. The durable sensor described in that patent has deformable pads creating conforming tissue contacting surfaces to which the emitters and photodetector are secured. The deformable pads are disposed in a hinged rigid housing that clips on the patient like a clothes pin. This relies on a clamping force to secure the sensor to the patient. The force of the sensor against the patient's tissue could reduce the flow of blood to that region. This exsanguination of the tissue beneath the sensor adversely affects pulse detection and analysis by suppressing the pulse in that portion of the tissue. As a result, the sensor site must typically be checked or moved every four hours to insure adequate perfusion. Because of its relatively large mass, however, the clamp design is more susceptible to signal-distorting motion artifact, i.e., differential motion between the sensor and the patient.

A third sensor design is described in U.S. Pat. No. 4,830,014. The conformable sensor described in that patent has emitters and a photodetector mounted in the same side of a flexible web. The web wraps around a portion of the patient's tissue (such as a finger) so that the light from the emitters must travel through the tissue before reaching the detector. The web attaches to the skin with an adhesive surface on the emitter and detector side of the web. Because of its relatively low mass and the adhesive, this sensor adheres closely to the patient's skin and minimizes the effects of motion artifact. In addition, its flexibility and use of adhesive to secure it minimizes the exsanguination caused by rigid sensors. Thus the sensor site typically only needs to be checked every eight hours. Conformable sensors, however, are typically restricted to one application due in part to a decrease in adhesive effectiveness with each application and in part to difficulties in cleaning and sterilization for reuse. Replacement of the sensor after only one use can make pulse oximetry expensive.

SUMMARY OF THE INVENTION

The present invention provides a pulse oximeter sensor that is designed to surround an appendage of the patient, such as a finger, toe or foot. The sensor has a reusable member which preferably includes a photodetector. A disposable, flexible member preferably contains the photoemitter and can be wrapped around the patient's appendage to secure it to the appendage and the reusable member. When secured, the photoemitter and photodetector end up on opposite sides of the appendage. The disposable member connects to the reusable member to establish electrical contact. The reusable member is connected to a cable which can be plugged into a sensor monitoring system.

In the preferred embodiment, the flexible member is a flexible adhesive web with arms extending laterally from a central portion. The reusable member is preferably a rigid housing with a deformable pad for contacting the appendage.

To attach the sensor to the patient, the flexible web is adhesively attached to one side of the patient's appendage, and the rigid housing is placed on the other side directly opposite the flexible web. The arms extend around the appendage to adhesively hold the conformable pad of the rigid housing against the appendage. By reducing the mass of the sensor and by adhesively attaching the emitters to the skin, this configuration minimizes motion artifact by reducing the relative movement between the sensor and the patient's skin experienced by previous clamp-type sensors. In addition, the flexible web and conformable surface of the rigid housing minimize exsanguination of the tissue beneath the sensor. Since the sensor relies on adhesion to secure it to the patient, the sensor site should not need to be checked as often as for a clamping-type sensor.

After use, the flexible web may be separated from the rigid housing, the rigid housing cleaned, and a new flexible web attached to the rigid housing. The fresh adhesive on the new flexible web provides a more reliable bond between the sensor and the patient than the adhesive on the previously-used web. In addition, since the flexible web covers four out of the five surfaces of the patient's appendage (including, when worn on the finger, the cuticle and subungual region), one time use of the flexible portion of the sensor minimizes cross-contamination between patients when the sensor is reused. Furthermore, because a portion of the sensor may be cleaned and reused, this new sensor design reduces the cost of using flexible sensors.

The electrical connection between the flexible web and the rigid housing is preferably made with a tab extending from the flexible web having conductive traces printed on it which connect to the photoemitter. The conductive traces are inserted into a channel in the back of the housing which is covered by a bridge. Underneath the bridge are a series of electrical contacts for making connection with the conductive traces. The tab contains an internal resilient foam which is compressed as it is inserted between the housing and the bridge, and exerts an outward force to maintain the tab in place and create an electrical connection between the conductive traces and the contacts.

For a fuller understanding of the nature and advantages of the invention, reference should be made to the ensuing detailed description taken in conjunction with the accompanying drawings.

DETAIL OF THE PREFERRED EMBODIMENT

Figure 1:
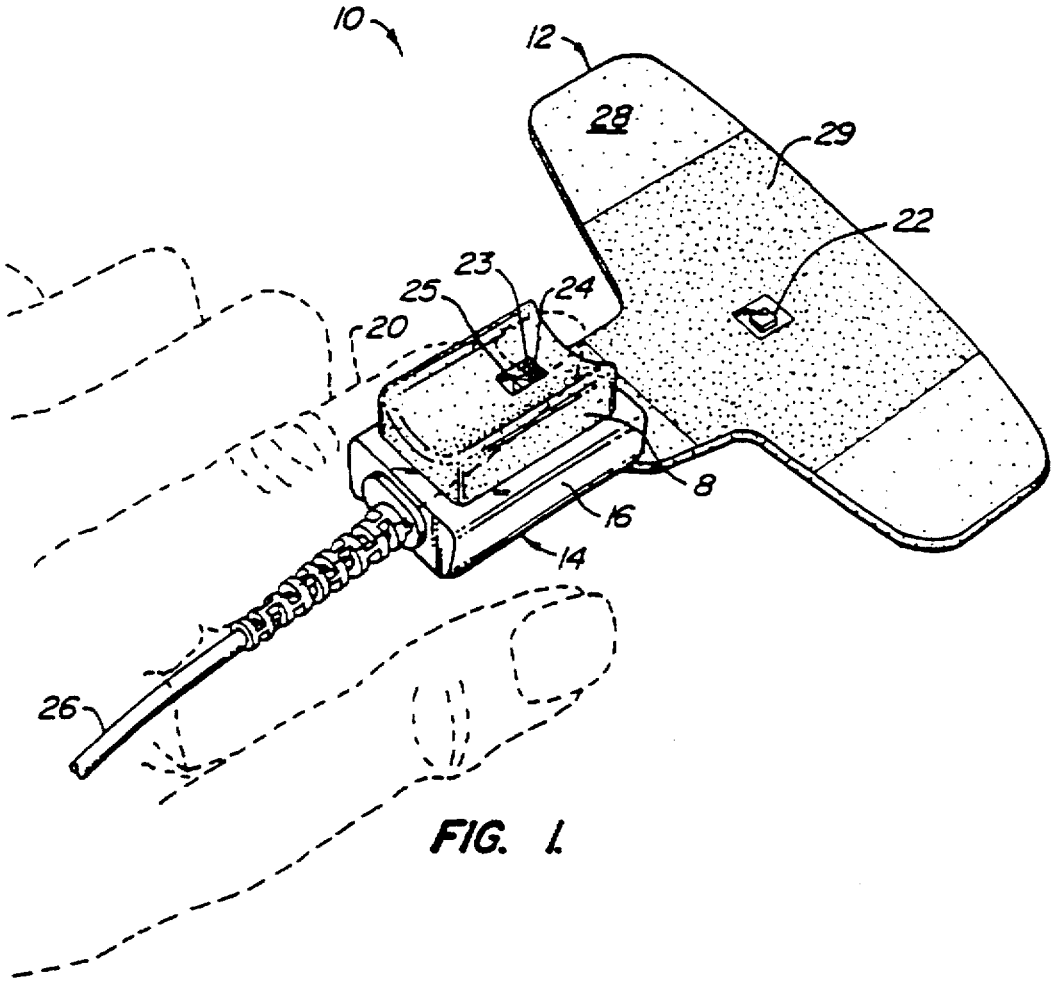
FIG. 1 is a perspective view of a sensor according to the present invention.

FIG. 1 shows a sensor 10 according to the present invention. Sensor 10 consists of a flexible, disposable webbing 12 and a reusable housing 14. Housing 14 includes a rigid portion 16 and a deformable pad 18. A patient's finger 20, shown in phantom, is shown placed on top of deformable pad 18.

Flexible web 12 includes a photoemitter 22, which preferably includes two photoemitters, one for red light and one for infrared light. A photodetector 24 is included in deformable pad 18. A copper grid 23 is disposed over photodetector 24. A transparent window 25 covers photodetector 24. All or substantially all of the portion of window 25 extending beyond photodetector 24 is colored black. In addition, a black area 29 is printed on the underside of foam layer 28. Grid 23, photodetector 24 and photoemitter 22 are electrically connected to a sensor monitoring system through conductors in a cable 26 connected to housing 14.

Grid 23 is a Faraday shield (electrostatic screen) connected to ground for reducing interference. The thin window 25 extends over the copper grid so that the grid will not bulge out pad 18. Before the black coating was added, shift errors in the data values were noticed. The black coating eliminated these errors. The reason is not certain, but the coating over the window may prevent reflections from most of the copper, while the black coating on the foam layer 28 may prevent light from being shunted through the foam layer to the detector, bypassing the finger.

Webbing 12 has a top foam layer 28 with an adhesive surface. Before use, this adhesive layer is covered with protective plastic (not shown), which is peeled off for use.

Figure 2:
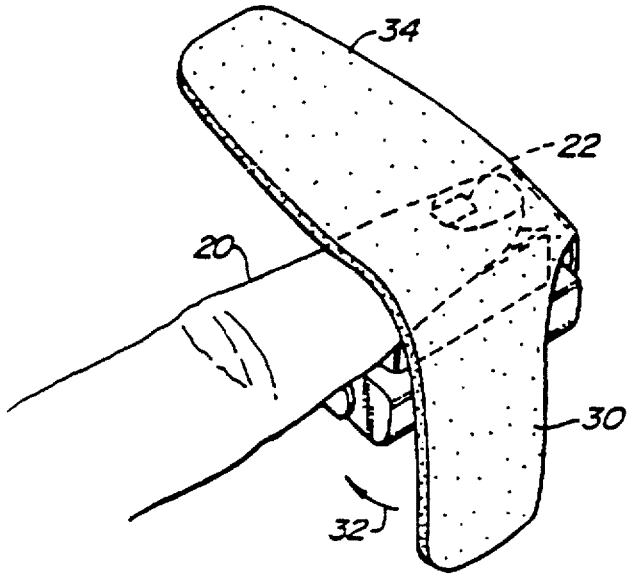
FIG. 2 is a perspective view of the sensor of FIG. 1 showing the flexible web being wrapped around a finger.

FIG. 2 illustrates how the flexible webbing 12 is bent over and attached to finger 20. A first arm 30 of the flexible web is wrapped around the side of housing 14 and will continue to be wrapped around its bottom in the direction of arrow 32. Similarly, the other arm 34 will be wrapped around finger 20 and housing 14. As can be seen, photoemitters 22, shown in phantom, are now on top of the finger, directly opposite photodetector 24, which is not visible in this view. As can be seen, only the bottom of finger 20 contacts deformable pad 18. At least the top of the finger will be adhered to by web 12. The sides and front may also be adhered to, depending on the shape of the finger and how the sensor is attached. The top is the portion which is most important to be adhering, since it contains the photoemitter which should not move relative to the finger. This provides a secure connection which reduces motion artifacts and puts the disposable, flexible portion in contact with most of the surfaces of the finger so that it is exposed to more contamination than the reusable portion.

Figure 3:
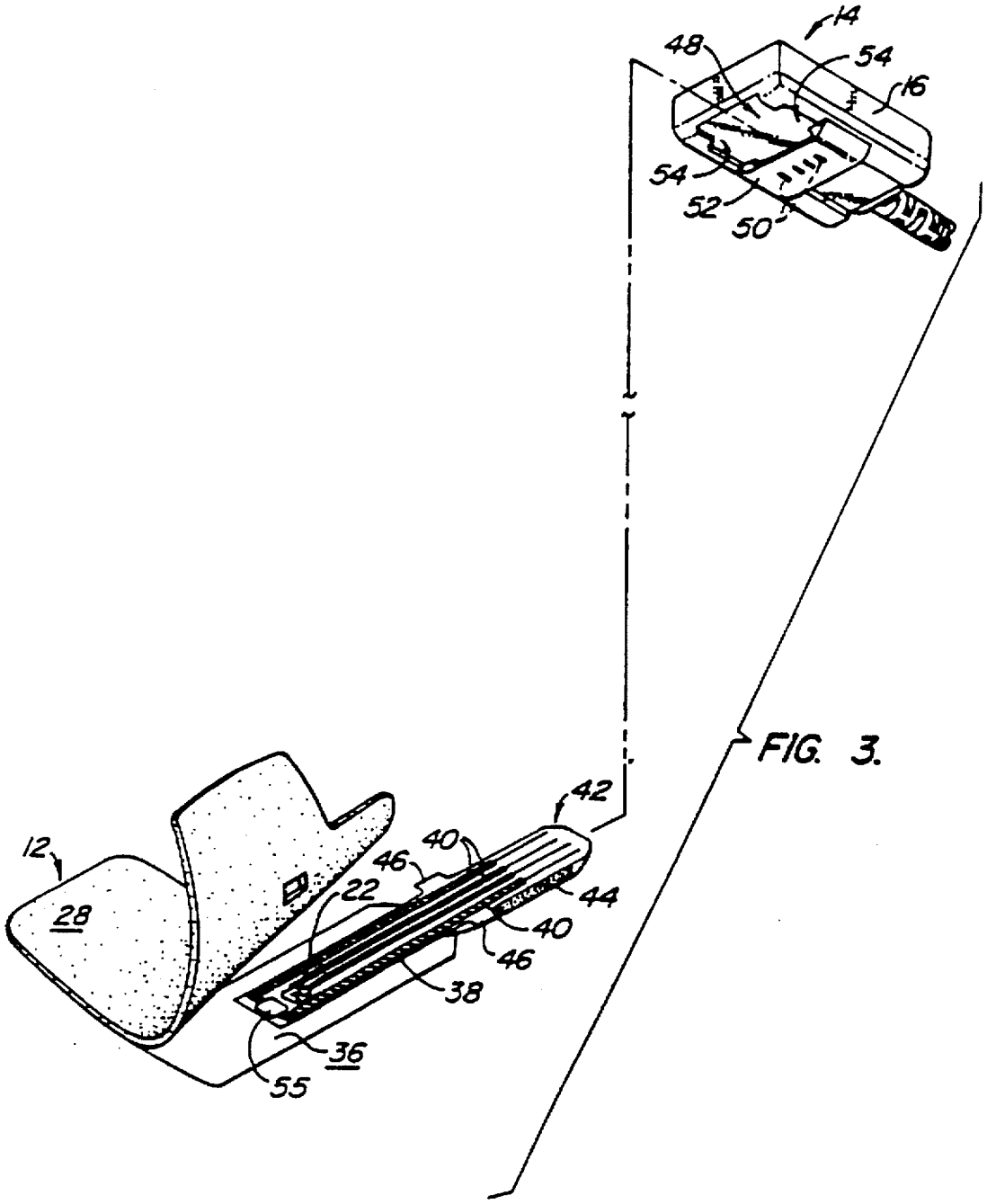
FIG. 3 is a perspective view of the separated disposable and reusable members of FIG. 1 illustrating how the connection is made.

FIG. 3 illustrates the electrical connection between flexible web 12 and rigid housing 14. FIG. 3 shows adhesive layer 28 partially peeled back from a web base 36. In between web base 36 and adhesive layer 28, an elongate plastic substrate 38 is placed, with a series of conductive traces 40 on its top surface. Two conductive traces connect to photoemitters 22, and two connect to a calibration resistor 55, described below. Elongate plastic substrate 38 forms a tail 42. Web base 36 can be just large enough to hold tail 42 to adhesive layer 28, as shown, or could conform to the shape of adhesive layer 28. Web base 36 has an adhesive surface for holding tail 42 to layer 28.

A compressible foam member 44 is placed between the halves of tail 42. In the preferred embodiment, the foam is made of Poron foam from Roger's Corp. A pair of tabs 46 extend from the top half of the tail having the conductive traces. The tabs and the foam member provide part of the attachment mechanism as explained below.

A channel 48 is formed on the bottom side of the rigid housing 16, opposite deformable pad 18. A series of electrical contacts 50 (shown in phantom) are located in the channel. The contacts are covered by a bridge 52 extending across the housing. A pair of grooves 54 are formed in the channel. The grooves are slightly larger than the tabs 46 on the flexible web.

To connect the flexible web to the rigid housing, the tail 42 of the flexible circuit is inserted into the space beneath bridge 52. As the tail moves forward, the plastic foam 44 compresses. As the tail's tabs 46 move over the channel's grooves 54, the spring action of the foam pushes the tabs into the grooves. The tabs and grooves ensure that the flexible circuit is not inserted too far and prevent inadvertent removal of the flexible circuit. The spring action of the foam also pushes one set of contacts against the other to enhance the electrical connection. In addition, the scraping action of one set of contacts against the other during insertion and withdrawal of the flexible circuit will help remove any oxidation or debris on the contacts. To remove, the tabs are lifted out of the grooves by pulling the flexible web away from the housing and the tail is withdrawn from the space beneath the bridge.

Cable 26 contains 6 wires. Two are connected to calibration resistor 55 through two of contacts 50 and conductive traces 40. Two are connected to photoemitters 22 through the other two of contacts 50 and conductive traces 40. The remaining two wires are connected to photodetector 24.

In the preferred embodiment, the plastic substrate is formed from white, substantially opaque polyester. White nylon may also be used, or a clear plastic. The adhesive may be white, with a clear window for the photoemitters.

The preferred embodiment of the sensor according to this invention includes an encoding/decoding system such as that described in U.S. Pat. No. 4,621,643. The flexible web supports an encoding resistor 55 in electrical communication with the monitor. As explained in that patent, the value of the resistor is selected to match the wavelengths of the red and infrared LED's. That patent also describes the necessary sensor monitoring electronics.

In an alternative embodiment, the sensor's photodetector may be mounted in the flexible web with the emitters and the encoding resistor mounted in the rigid housing.

In the preferred embodiment, the rigid housing is made from injection molded polycarbonate. Alternatively, injection molded ABS plastic may be used. U.S. Pat. No. 4,685,464 contains additional details on construction of a rigid housing and deformable pad including the placement of the photodetector.

As will be understood by those familiar with the art, the present invention may be embodied in other specific forms without departing from the spirit or essential characteristics thereof. For example, the compression effect of foam 44 could be obtained instead by making bridge 52 a spring-action clip, which is opened by holding one end down during insertion and then released, with a spring on the clip holding the tab in place. Other variations in the way electrical contact is made are also possible. Instead of the adhesive layer, the flexible portion could be attached to the finger and rigid housing using velcro or other securing mechanisms. The flexible web could be made of foil or other color materials than white or clear. The sensor could be a surface sensor, with adhesive for reducing motion artifact on the disposable portion. Accordingly, the disclosure of a preferred embodiment of the invention is intended to be illustrative, but not limiting, of the scope of the invention which is set forth in the following claims.

What is claimed is:

1. A sensor for attaching to a patient for electrooptical measurement of blood characteristics, comprising:

a reusable member including a first electronic means for emitting or detecting electromagnetic radiation;

conducting means, connected to said reusable member, for electrically connecting said first electronic means to an external sensor monitoring system;

a disposable, flexible member including a second electronic means for detecting electromagnetic radiation emitted by said first electronic means or emitting electromagnetic radiation to be detected by said first electronic means;

means for removably coupling said flexible member to said reusable member to provide a connection between said second electronic means and said conducting means; and means for securing said disposable, flexible member and reusable member to said patient.

2. The sensor of claim 1 wherein said means for securing comprises an adhesive on said disposable, flexible member.

3. The sensor of claim 1 wherein said second electronic means is at least one photoemitter.

4. The sensor of claim 1 wherein said means for removably coupling comprises a tail extending from said disposable, flexible member having at least one exposed first electrical conductor, at least one exposed second electrical conductor extending from said reusable member, and a bridge means connected to said reusable member and extending across said second electrical conductor for allowing said tail to be inserted between said bridge means and said second conductor.

5. The sensor of claim 4 wherein said tail includes resilient means for applying force between said second conductor and said bridge means to hold said tail in place.

6. The sensor of claim 1 wherein said reusable member comprises a rigid housing and a deformable means, attached to said housing, for securely gripping and complying to an appendage of said patient.

7. The sensor of claim 1 wherein said second electronic means comprises a red light photoemitter and an infrared photoemitter.

8. The sensor of claim 7 wherein said first electronic means comprises a photodetector.

9. The sensor of claim 1 wherein said means for securing attaches said sensor to an appendage of said patient so that said first electronic means is on an opposite side of said appendage from said second electronic means.

10. The senor of claim 1 further comprising a black coating on said flexible member around said second electronic means.

11. The sensor of claim 1 further comprising:

an electrostatic screen adjacent said first electronic means; and a thin film covering said first electronic means and at least a portion of said electrostatic screen, said film being transparent over said first electronic means and opaque over said portion of said electrostatic screen.

12. A sensor for attaching to an appendage of a patient for electrooptical measurement of blood characteristics, comprising:

a reusable member including a first electronic device for emitting or detecting light;

conducting means for electrically connecting said first electronic device to an external sensor monitoring system;

a disposable, flexible member including a second electronic device for detecting light emitted by said first electronic device or emitting light to be detected by said first electronic device;

a tail extending from said disposable, flexible member having at least one exposed first electrical conductor, at least one exposed second electrical conductor extending from said reusable member, and a bridge connected to said reusable member and extending across said second electrical conductor to allow said tail to be inserted between said bridge and said second conductor;

means for securing said disposable, flexible member to said appendage and said reusable member so that said first electronic device is on an opposite side of said appendage from said second electronic device.

13. The sensor of claim 12 wherein said means for securing comprises an adhesive on said disposable, flexible member.

14. The sensor of claim 12 wherein said second electronic device is a photoemitter.

15. The sensor of claim 12 wherein said tail includes resilient means for applying force between said second conductor and said bridge to hold said tail in place.

16. A sensor for attaching to an appendage of a patient for electrooptical measurement of blood characteristics, comprising:

a reusable member including a photodetector;

conducting means, connected to said reusable member, for electrically connecting said photodetector to an external sensor monitoring system;

a disposable, flexible member including at least one photoemitter for emitting light to be detected by said photodetector;

means for removably coupling said flexible member to said reusable member to provide a connection between said photoemitter and said conducting means; and an adhesive coating on said disposable, flexible member for securing said disposable, flexible member to said appendage and said reusable member so that said photodetector is on an opposite side of said appendage from said photoemitter.

17. A sensor for attaching to an appendage of a patient for electrooptical measurement of blood characteristics, comprising:

a reusable member including at least one photodetector, said reusable member including a rigid housing and a deformable means, attached to said housing, for securely gripping and complying to said patient's appendage;

conducting means, connected to said reusable member, for electrically connecting said photodetector to an external sensor monitoring system;

a disposable, flexible member including a red light photoemitter and an infrared photoemitter for emitting light to be detected by said photodetector;

a tail extending from said disposable, flexible member having at least one exposed first electrical conductor;

at least one exposed second electrical conductor extending from said rigid housing;

a bridge connected to said rigid housing and extending across said second electrical conductor to allow said tail to be inserted between said bridge and said second conductor;

resilient means, coupled to said tail, for applying force between said second conductor and said bridge to hold said tail in place; and an adhesive coating on said disposable, flexible member for securing said disposable, flexible member to said appendage and said reusable member so that said photoemitters are on an opposite side of said appendage from said photodetector.

*18. A sensor for attaching to a patient for electrooptical measurement of blood characteristics, comprising:*

*a disposable, flexible member having a plurality of conductors disposed on a substrate and including at least one electronic means for emitting or detecting electromagnetic radiation, said at least one electronic means being connected to at least one of said conductors disposed on said substrate;*

*conducting cable means for electrically connecting said electronic means to an external sensor monitoring system;*

*means for releasably connecting said flexible member conductors to said conducting cable means to provide a connection between said electronic means and said conducting cable means; and*

*means for securing said flexible member to said patient.*

*19. The sensor of claim 18, wherein said means for securing comprises an adhesive connected to said substrate.*

*20. The sensor of claim 18, wherein said at least one electronic means is a photoemitter.*

*21. The sensor of claim 18, wherein said at least one electronic means is a photodetector.*

*22. The sensor of claim 18, wherein an end of said conducting cable means opposite said releasably connecting means is adapted to be connected to an oximeter monitor.*

*23. The sensor of claim 18, wherein said blood characteristics include arterial oxygen saturation.*

*24. The sensor of claim 18, wherein said substrate is elongated and flexible.*

*25. The sensor of claim 18, wherein said plurality of conductors, include a plurality of contacts on a surface of said substrate which can be connected to said releasably connecting means for electrically connecting said conducting cable means to said at least one electronic means.*

*26. The sensor of claim 18, wherein said plurality of conductors comprise a plurality of conductive traces disposed on said substrate.*

*27. The sensor of claim 26, wherein said traces comprise printed traces.*

* * * * *